United States Patent [19]

Stec, III et al.

[11] Patent Number: 5,808,099

[45] Date of Patent: Sep. 15, 1998

[54] ADNAZ, COMPOSITIONS AND PROCESSES

[75] Inventors: Daniel Stec, III, Hackettstown; Paritosh R. Dave, Bridgewater, both of N.J.

[73] Assignee: The United States of America as represented by the Secretary of the Army, Washington, D.C.

[21] Appl. No.: 440,947

[22] Filed: May 15, 1995

[51] Int. Cl.[6] .................................................. C07D 205/04
[52] U.S. Cl. .............................................................. 548/953
[58] Field of Search ............................................... 548/953

[56] References Cited

U.S. PATENT DOCUMENTS 3,037,019  5/1962  Testa et al. ............................... 548/953
5,395,945  3/1995  Hiskey ..................................... 548/953

OTHER PUBLICATIONS

Axenrod, T. et al., "Synthesis of 1,3,3–Trinitroazetidine," *Tetrahedron Letters*, vol. 34, No. 42, pp. 6677–6680, 1993.

*Primary Examiner*—Jacqueline Haley
*Attorney, Agent, or Firm*—Edward Goldberg; John E. Callaghan; Michael C. Sachs

[57] ABSTRACT

ADNAZ, N-acetyl, 3,3 dinitroazetidine, is a new compound and this invention provides the compound, its compositions, preparation and uses. As a compound, it forms a eutectic with TNAZ. It can be used to prepare other compounds. It can be readily nitrated to remove the acetyl group and form TNAZ.

6 Claims, 2 Drawing Sheets

X-Ray Structure of ADNAZ

Crystal Density 1.55 g/cc

ADNAZ, COMPOSITIONS AND PROCESSES

STATEMENT OF GOVERNMENT INTEREST

The invention described herein may be manufactured, used and licensed by or for the United States Government for governmental purposes without the payment to us of any royalties thereon.

STATEMENT OF RELATED APPLICATIONS

This application is related to the U.S. patent applications described below; the applications have been filed simultaneously with this application. The applications are:

DAR 4-94B Ser. No. 08/440,946 May 15, 1995 pending
DAR 4-94C Ser. No. 08/440,945 May 15, 1995 pending
DAR 4-94D Ser. No. 08/441,511 May 15, 1995 allowed
DAR 4-94E Ser. No. 08/441,512 May 15, 1995 pending

BACKGROUND OF INVENTION

This invention relates to a chemical compound, processes for making the compound, products using the compound and processes of using the compound. Generally, the field of energetic materials use compounds having N-Nitro, C-Nitro and O-Nitro structures. A material under current evaluation as an energetic material for explosives and propellants is 1,3,3-trinitroazetidine, known as TNAZ. This has a high energy density and other properties which are of importance in explosives and propellants. The present invention provides a new chemical compound that can be used to make TNAZ. Also, it can be combined with TNAZ to form compositions that improve the versatility and uses of TNAZ.

SUMMARY OF INVENTION AND FIGURES

Overall, the invention makes available a high density, high melting point, thermally stable compound having a small heterocyclic nitrogen ring of four atoms that may also contain C-nitro or other functional groups. The particular compound is N-acetyl-3,3-dinitroazetidine and is commonly known as ADNAZ. This compound, ADNAZ, is useful in itself and as an intermediate to prepare TNAZ.

The processes of this invention for preparing ADNAZ and for preparing TNAZ from ADNAZ are advantageous in that the reaction conditions give improved yields and readily recoverable products. The compositions of the invention include eutectics of ADNAZ and TNAZ which have low melting points in the range of 78 degrees C. This is a benefit in practicing melt casting processes and in fabricating articles which use TNAZ and ADNAZ as explosive charges or propellant loads. These compositions may contain other ingredients such as high melting energetic materials.

BRIEF DESCRIPTIONS OF THE DRAWINGS

The Figures illustrate several aspects of the invention. FIG. 1 illustrates the chemical formula and X-ray structure of ADANZ. FIG. II illustrates a method for preparing ADNAZ and a method for preparing TNAZ from ADNAZ.

DETAILED DESCRIPTION OF THE INVENTION AND FIGURES

The practice of the invention and the compounds, processes and products of the invention are further described by reference to the following detailed description of the invention.

Figure 1:
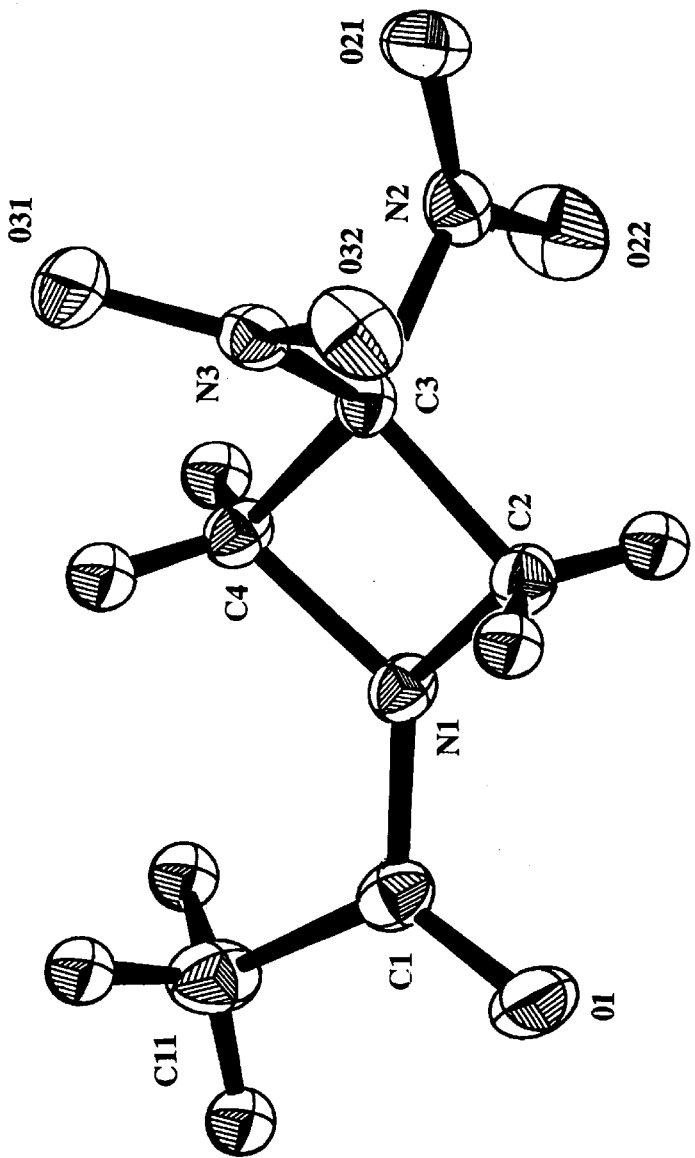
Figure 2:
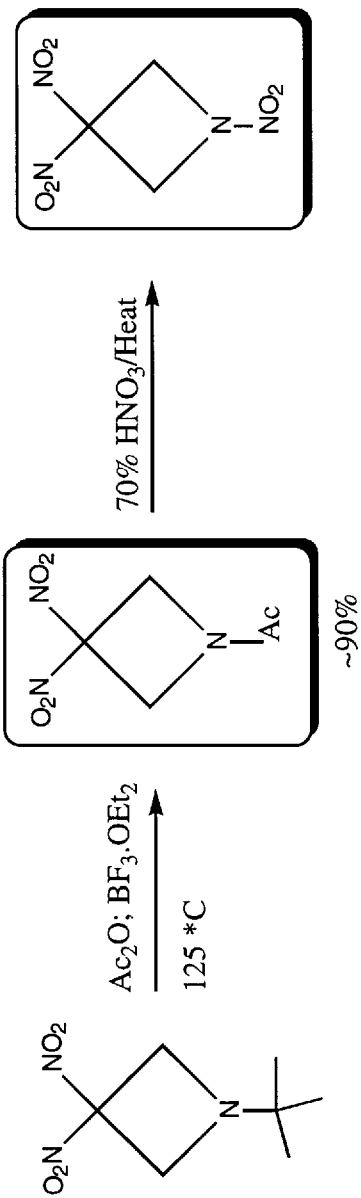

ADNAZ is a white or colorless crystalline solid with a melting point of 114.8 degrees C. It is soluble in acetone and other organic solvents such as methylene chloride. FIG. I shows the structural formula and the X-ray structure of ADNAZ. This is consistent with NMR analysis. In FIG. 1, the X-Ray structure shows the spatial arrangement of the carbon, oxygen and nitrogen atoms relative to the plane of the azetidine ring. The calculated crystal density is 1.55 g/cc.

As shown in FIG. I, ADNAZ is an azetidine with an acetyl group connected to the aza nitrogen atom and two nitro groups at the 3 position of the ring. ADNAZ can be an intermediate to other compounds because the acetyl group on the ring nitrogen may be easily removed and replaced with other groups.

FIG. II shows a process where ADNAZ is prepared from N-tertbutyl,3,3-dinitroazetidne and where the ADNAZ is then converted to TNAZ.

Among the properties of ADNAZ that make it suitable for use as an energetic material are that is has a crystal density of 1.55 g/cc and it is relatively insensitive to detonation on impact. Therefore, it is suitable as an ingredient in energetic materials, either by itself or with other compounds.

ADNAZ forms solutions with TNAZ. Also it has the additional advantage that it forms a eutectic with TNAZ. The eutectic occurs at about 66 Mol % TNAZ/34mol % ADNAZ. It has a melting point of about 78.6 degrees C. This is a relatively low melting point for an energetic material and is in the range where it can be melt cast into articles. This temperature range allows the forming of articles by shaping in situ an explosive charge or propellant load. In one example, shaped charge antitank weapons can be prepared by taking advantage of this eutectic property. Another feature is to use the low melting eutectic as an energetic carrier for higher melting energetic materials such as HMX and the like.

As shown in FIG. II, ADNAZ is readily prepared by an acylative dealkylation in which an azetidine with a tertiary alkyl on the aza nitrogen is reacted with a catalytic amount of a Lewis acid catalyst in the presence of an electrophile. The tertiary alkyl group leaves and is replaced by the acetyl group. It is important to note that the four membered ring remains intact. The particular reaction conditions are as shown in FIG. II.

ADNAZ can be used to prepare other compounds. FIG. II also illustrates the preparation of TNAZ from ADNAZ. ADNAZ has two nitro groups. The acetyl group attached to the nitrogen atom can be replaced with other groups. For the preparation of TNAZ, the acetyl group is replaced by a nitro group. Any conventional nitrating agent can be used. Aqueous nitric acid and heat is enough to convert the ADNAZ to TNAZ. These are mild and easily controlled conditions. Overall, FIG. II shows the preparation of the ADNAZ and the conversion of the ADNAZ to TNAZ. While the two processes can be carried out together, it is clear that each can be carried out separately.

It is intended that the invention includes the equivalent compounds, products, reaction conditions, reaction steps, reaction processes and variations of such equivalents as are commonly practiced in this field as well as the specific embodiments described above.

We claim:

1. The compound N-acetyl, 3,3-dinitroazetidine.
2. A process for the preparation of 1,3,3-trinitroazetidine comprising reacting N-acetyl 3,3-dinitroazetidine with a nitrating agent.
3. The process of claim 2 where the nitrating agent is nitric acid.
4. A composition comprising a solution of N-acetyl-3,3-dinitroazetidine and 1,3,3-trinitroazetidine.

5. The composition of claim 4 wherein the N-acetyl-3,3-dinitroazetidine and 1,3,3-trinitro-azetidine are present as a eutectic and are in a mol ratio of 34 mol % N-acetyl-3,3-dinitroazetidine and 66 mol % of 1,3,3-trinitroazetidine.

6. The composition of claim 5 having a normal melting point of about 78.6 degrees C.

* * * * *